(12) United States Patent
Yamaguchi

(10) Patent No.: US 7,625,535 B2
(45) Date of Patent: Dec. 1, 2009

(54) STERILIZER

(75) Inventor: Koji Yamaguchi, Sakata (JP)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 11/879,073

(22) Filed: Jul. 16, 2007

(65) Prior Publication Data
US 2008/0152557 A1    Jun. 26, 2008

(30) Foreign Application Priority Data
Jul. 14, 2006   (JP)   ............... 2006-194838

(51) Int. Cl.
*A61L 2/07*   (2006.01)
(52) U.S. Cl. .................. 422/296; 422/26; 422/292; 422/295
(58) Field of Classification Search ............ 422/26, 422/292, 295, 296
See application file for complete search history.

(56) References Cited

U.S. PATENT DOCUMENTS

| | | | | |
|---|---|---|---|---|
| 3,431,902 A | * | 3/1969 | Vischer, Jr. ............... | 126/20 |
| 5,906,800 A | * | 5/1999 | Napierkowski et al. ...... | 422/298 |
| 6,048,494 A | * | 4/2000 | Annapragada ............... | 422/33 |
| 6,537,509 B2 | * | 3/2003 | Saint-Martin et al. ....... | 422/297 |
| 7,282,176 B2 | * | 10/2007 | Glachet et al. .............. | 422/28 |

\* cited by examiner

*Primary Examiner*—Sean E Conley
(74) *Attorney, Agent, or Firm*—Casimir Jones, S.C.

(57) ABSTRACT

A sterilizer, which is not large, but includes a hermetic container capable of defining a sealed space therein without being closed by a locking device from the outside, is disclosed. The sterilizer includes a hermetic container, which defines therein a steam chamber for conducting the heat sterilization of objects. The hermetic container includes a steam supply unit for supplying hot steam to the steam chamber, and an opening/closing unit for closing the steam chamber. The opening/closing unit includes an opening for passing the objects and a door for closing the opening from the inside of the chamber. The door is moved to come into contact with the opening from the inside, and the steam pressure inside the steam chamber is increased by the pressurized steam from the steam supply unit, so that the door can come into close contact with the opening, thus hermetically sealing the steam chamber.

7 Claims, 11 Drawing Sheets

(B)            (A)            (C)

FIGURE 2
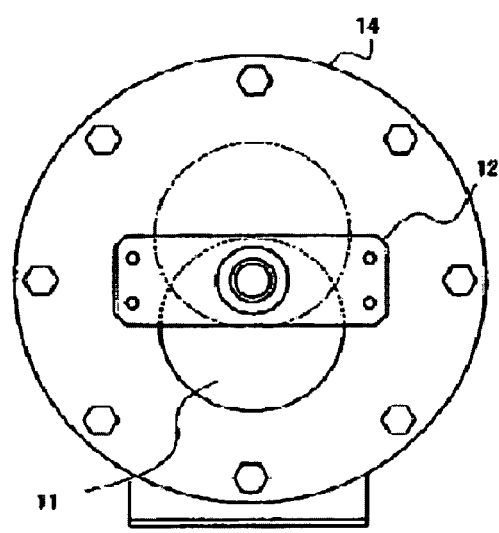
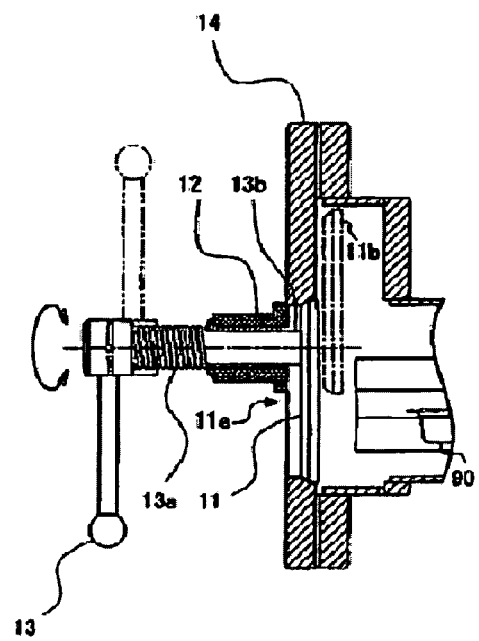
(B)                  (A)

| 1 cycle | 1 | valve 203 | closed | —S201 |
|---|---|---|---|---|
| | 2 | valve 202 | opened | —S202 |
| | 3 | degassing | | —S203 |
| | 4 | valve 204 | closed | —S204 |
| | 5 | Suction of steam | | —S205 |
| | 6 | valve 202 | closed | —S206 |
| | 7 | valve 204 | opened | —S207 |
| | 8 | Discharge of steam | | —S208 |
| | 9 | valve 202 | opened | |
| | 10 | degassing | | |
| | 11 | valve 204 | closed | |
| | 12 | Suction of steam | | |
| | 13 | valve 202 | closed | |
| | 14 | valve 204 | opened | |
| | 15 | Discharge of steam | | |

Fig. 12
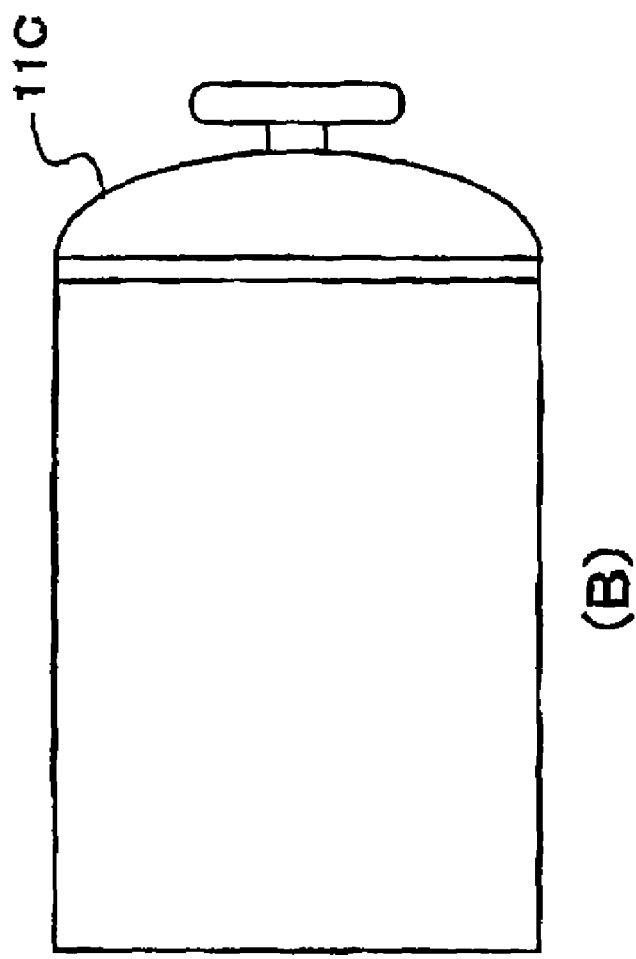
(B)
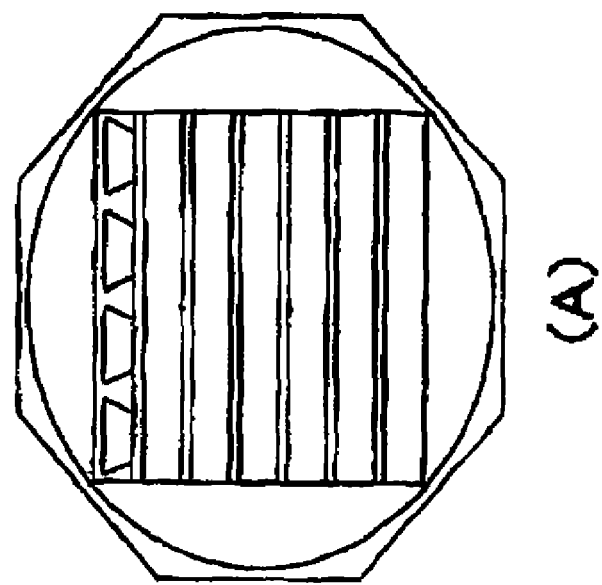
(A)

STERILIZER

BACKGROUND OF THE INVENTION

1. Field of the Invention

The present invention relates, in general, to sterilizers for conducting the heat sterilization of objects and, more particularly, to a sterilizer having a hermetic container for sterilizing objects contained therein.

2. Description of the Related Art

In the related art, as an example of a sterilizer for conducting the heat sterilization of objects, such as food stuffs, a large-sized kettle, which contains food stuffs therein and the door of which is locked from the outside, as shown in FIGS. 12A and 12B, is known.

However, the large-sized kettle used as a conventional sterilizer is problematic in that a temperature difference is generated between areas in the kettle body and in that it takes too long for the temperature in the kettle body to increase to the point capable of sterilizing the food stuffs. Further, when the interior of the kettle body is pressurized to lock the door of the kettle body from the outside after the opening of the kettle body has been closed using the door, a mechanical load may be easily applied to the locked part between the edge of the door and the opening of the kettle body, necessitating an increase in the size of the locking device, thus reducing the operational efficiency of the sterilizer.

Therefore, to seal food stuffs in a sterilizer, a technique, in which small-sized first and second chambers are closely defined in the upper and lower parts of the sterilizer and thus form sealed spaces in the sterilizer, was proposed (Patent Document 1).

According to the technique disclosed in Patent Document 1, the kettle body is configured as a small-sized body, so that the temperature variation in the kettle body can be restricted and the time period required to increase the temperature to a desired point can be reduced (Reference Document: Japanese Patent Laid-open Publication No. Hei. 10-99061).

However, in the technique disclosed in Patent Document 1, the first and second chambers must be compressed and connected to each other from the outside so as to define the sealed spaces in the sterilizer, so that the technique still causes the problem experienced in the large-sized kettles used as the conventional sterilizers.

Further, to define the first and second chambers in the sterilizer, the body of the sterilizer must be configured as a large-sized body. Further, because a large-sized drive part must be provided in the sterilizer, the sterilizer is subjected to wear.

SUMMARY OF THE INVENTION

Accordingly, the present invention has been made keeping in mind the above problems occurring in the related art, and provides a sterilizer, which is not large, but includes a hermetic container capable of defining a sealed space therein without being closed from the outside using a locking device.

In an aspect, the present invention provides a sterilizer comprising a hermetic container, which defines therein a steam chamber for conducting the heat sterilization of objects contained therein, wherein the hermetic container includes: a steam supply unit for supplying hot steam having a predetermined pressure to the steam chamber; and at least one opening/closing unit for hermetically closing the steam chamber, wherein the opening/closing unit includes an opening for passing the objects therethrough and a door for closing the opening from the inside of the steam chamber, wherein the door is moved so that it comes into contact with the opening from the inside of the steam chamber and the steam pressure inside the steam chamber is increased by the steam supply unit, so that the door can be brought into close contact with the opening, thereby hermetically sealing the steam chamber.

According to the above-mentioned construction, the door of the sterilizer is brought into close contact with the opening from the inside of the steam chamber by the steam pressure increased due to the steam having a predetermined pressure supplied to the steam chamber from the steam supply unit, so that the steam chamber can be hermetically sealed.

The objects may be a variety of goods, such as retorted food or hygienic goods, which are required to be subjected to heat sterilization.

In the present invention, the opening may be defined by a tapered circular edge, the diameter of which is reduced in the direction from the inside to the outside of the steam chamber, and the door may comprise a frusto-conical part at an end thereof, the frusto-conical part of the door coming into close contact with the tapered circular edge of the opening.

According to the above-mentioned construction, the door having the frusto-conical part comes into close contact at the frusto-conical part with the tapered circular edge of the opening, which has a diameter reduced in the direction from the inside to the outside of the steam chamber. Thus, the opening of the container of the sterilizer can be hermetically sealed.

Further, the tapered circular edge of the opening, with which the frusto-conical part of the door comes into close contact, may be provided with a sealing member, such as an O-ring, for increasing the sealing effect of the sterilizer. Further, when the edge of the opening is not tapered, a sealing member, such as an O-ring, may be provided around the edge of the door, which has a diameter larger than that of the opening.

In the sterilizer, the opening/closing unit may be manipulated outside the hermetic container so as to open or close the opening with the door.

According to the above-mentioned construction, the door can be opened or closed by manipulating it outside the container body.

In the sterilizer, the hermetic container may comprise a cylindrical container body and an end plate, which is provided on each end of the cylindrical container body and includes the opening/closing unit for covering the end of the container body, wherein the objects are put into the container body through the opening of one of two opening/closing units provided in opposite ends of the container body, and are taken out of the container body through the opening of a remaining opening/closing unit.

According to the above-mentioned construction, the objects can be rectilinearly put into or taken out of the hermetic container through the opening provided in the end plate.

Further, the container body may be configured to have a desired shape, such as a polygonal column shape, without being limited to the cylindrical shape. Further, the length of the container body can be freely determined according to the size and number of the objects to be put into the hermetic container. Further, to sterilize predetermined portions of a plurality of objects at the same time, the sterilizer can be configured such that it receives therein the predetermined portions of the objects at the same time.

The sterilizer may further comprise an inlet unit for sequentially putting the objects into the steam chamber through the opening of one of the opening/closing units and an outlet unit for sequentially discharging the objects from the steam chamber through the opening of the remaining opening/closing unit, wherein the opening/closing units are operated in conjunction with both the inlet unit and the outlet unit, thus opening or closing the respective openings.

According to the above-mentioned construction, the sterilizer can be automated by opening or closing the opening in conjunction with both the inlet unit and the outlet unit, so that the sterilizer can continuously execute the pressure sterilization of objects.

Further, the inlet unit and the outlet unit may be freely designed as long as the inlet and outlet units can continuously put objects into the steam chamber or remove them therefrom. For example, the inlet and outlet units may be configured as a belt conveyor system or another type of feed system.

Further, the door may be supported by a rotating shaft, which passes through the opening, such that the door is rotatable and movable inwards and outwards, wherein the end of the rotating shaft is eccentrically connected to the door.

According to the above-mentioned construction, the door is eccentrically and rotatably connected to the end of the rotating shaft, which passes through the end plate, so that the opening can be easily opened or closed by rotating the rotating shaft. Further, the rotating shaft passes through the opening, so that the size of the opening, which may weaken the seal of the steam chamber of the hermetic container, can be reduced.

Further, the rotating shaft may be provided with a spring, which elastically biases both the rotating shaft and the door in a direction from the inside to the outside of the hermetic container. Further, an actuating lever may be provided on the rotating shaft to allow a user to manually open or close the door. The opening/closing unit may be provided with an appropriate machine, such as a motor, for automatically opening or closing the door.

According to the present invention, steam having a predetermined pressure is supplied to the hermetic container from the steam supply unit, so that the steam pressure inside the steam chamber is increased and the increased steam pressure pushes the door onto the edge of the opening outwards, thus hermetically sealing the steam chamber. Therefore, the present invention can provide a sterilizer, which is not large, but includes a hermetic container capable of defining a sealed space therein without being closed by a locking device from the outside.

BRIEF DESCRIPTION OF THE DRAWINGS

The above and other objects, features and other advantages of the present invention will be more clearly understood from the following detailed description when taken in conjunction with the accompanying drawings, in which:

FIGS. 2A and 2B are enlarged views illustrating the construction and operation of a door unit of the sterilizer according to the embodiment of the present invention;

FIGS. 12A and 12B are views illustrating an example of a conventional sterilizer.

DETAILED DESCRIPTION OF THE INVENTION

Hereinbelow, a sterilizer according to an embodiment of the present invention will be described with reference to the accompanying drawings.

First Embodiment

Figure 1:
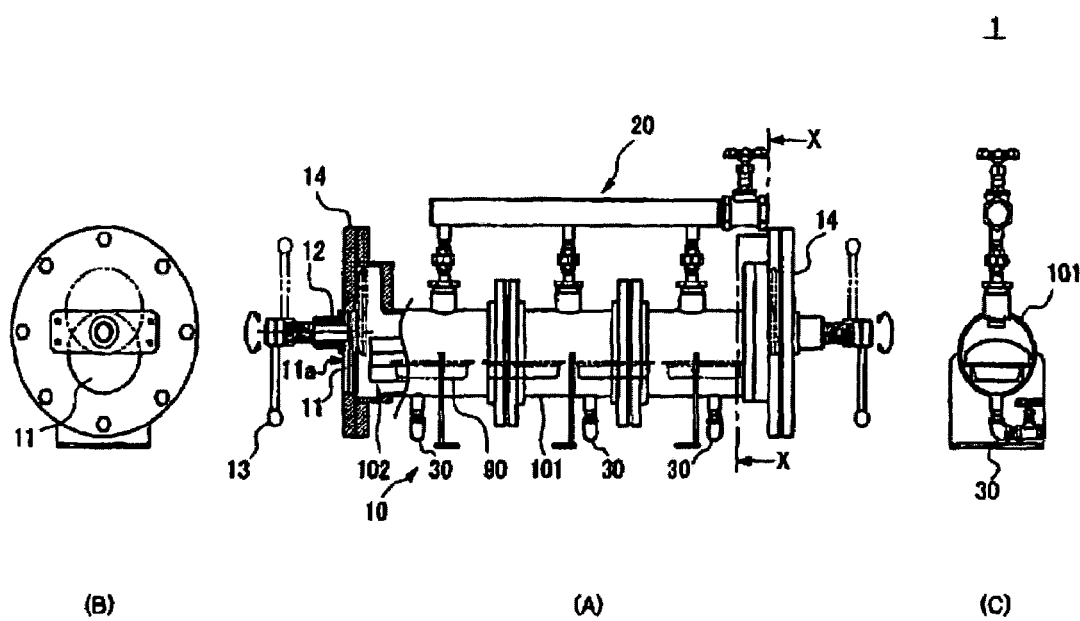
FIGS. 1A, 1B and 1C are views illustrating the construction of a sterilizer according to an embodiment of the present invention.
Figure 3:
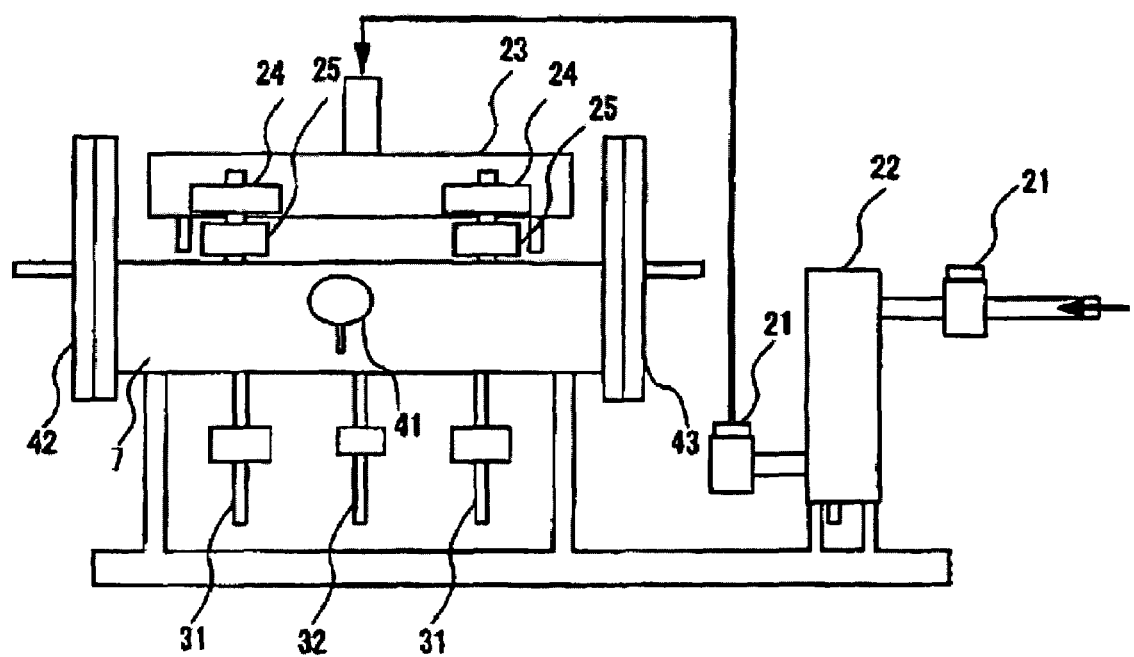
FIG. 3 is a diagram schematically illustrating the construction of the sterilizer according to the embodiment of the present invention.

FIGS. 1A through 1C are views illustrating the construction of a sterilizer 1 according to an embodiment of the present invention, in which FIG. 1A is a front view of the sterilizer, FIG. 1B is a left side view of FIG. 1A, and FIG. 1C is a sectional view taken along line X-X of FIG. 1A. FIG. 2A is an enlarged view of an important part of FIG. 1A. FIG. 2B is a left side view of FIG. 2A. FIG. 3 is a diagram schematically illustrating the construction of the sterilizer 1 according to the embodiment of the present invention.

As shown in FIGS. 1A through 1C, the sterilizer 1 according to the first embodiment of the present invention includes a hermetic container 10 defining a steam chamber 102 therein, a steam supply unit 20 functioning as a steam supply means for supplying hot steam into the hermetic container 10, a plurality of pressure regulators 30, and a door 11, which constitutes an opening/closing unit for opening or hermetically closing an opening 11a of the hermetic container 10 from the inside of the container 10.

Further, as shown in FIG. 1A, the hermetic container 10 comprises a cylindrical container body 101 and two end plates 14, which are provided on the opposite ends of the cylindrical container body 101 and include the respective opening/closing units for covering the respective ends of the container body 10. Objects to be sterilized are put into the container body 101 through the opening 11a of one of the two opening/closing units, and the sterilized objects are taken out of the container body 101 through the opening (not shown) of the remaining opening/closing unit.

As shown in FIG. 2A, the opening 11a, which is opened or closed by the door 11, is defined by a tapered circular edge, the diameter of which is reduced in the direction from the inside to the outside of the container body 101. The door 11 comprises a circular body having a frusto-conical part, and is eccentrically connected to an inner end of a rotating shaft 13b.

Described in detail, the door 11 is eccentrically connected to the inner end of the rotating shaft 13b, which passes through the opening 11a of the end plate 14, such that the door 11 can be eccentrically rotated by the rotating shaft 13b. Thus, when an actuating lever 13, which is mounted to the outer end of the rotating shaft 13b, is rotated in one direction, the rotating shaft 13b eccentrically rotates the door 11 in the same direction, so that the door 11 can open or close the opening 11a.

The rotating shaft 13b, which is eccentrically mounted at the inner end thereof to the door 11, rotatably passes both through the opening 11a and through a bushing 12. In the above state, the rotating shaft 13b passes through the bushing 12 such that the door 11 can be eccentrically rotated, and, at the same time, moved inwards and outwards.

When it is required to close the opening 11a, the user rotates the actuating lever 13 in the direction such that the door 11 comes into close contact with the tapered circular edge of the opening 11a. In the above state, the rotating shaft 13b has been moved outwards, so that a spring 13a, which is provided around the shaft 13b, elastically pulls the door 11 outwards. Thus, the door 11 is elastically biased outwards and brought into close contact with the tapered circular edge of the opening 11a of the end plate 14, thus sealing the junction between the door 11 and the tapered circular edge of the opening 11a.

When it is required to open the opening 11a, the user rotates the actuating lever 13 in the opposite direction. Thus, the door 11 is eccentrically rotated along the tapered circular edge of the opening 11a and is moved inwards. When the rotating shaft 13b has been rotated at an angle of 180 degree, the door 11 reaches an inside location 11b.

Thus, the opening 11a is opened and allows the user to put objects 90 into the container 10 or remove them therefrom.

Here, the rotating shaft 13b passes through the opening 11a, so that the size of the opening 11a, which may weaken the seal of the steam chamber 102 of the hermetic container 10, can be reduced.

Further, because steam having a predetermined pressure is supplied into the steam chamber 102 of the hermetic container 10 from the steam supply unit 20 in the state in which the opening 11a has been completely closed, the door 11 is pneumatically pushed outwards by the increased steam pressure of the steam chamber 102. Thus, the door 11 can be retained in close contact state with the edge of the opening 11a, and reliably seals the steam chamber 102.

As described above, the door 11 of the sterilizer 1 according to the first embodiment of the present invention is brought into close contact with the tapered circular edge of the opening 11a of the hermetic container 10 from the inside of the container 10, and seals the steam chamber 102. Thus, the door 11 of the present invention is different from the door 11c of a conventional sterilizer, which is closed by forcibly manipulating it from the outside while overcoming the high pressure of the steam chamber, as shown in FIGS. 12A and 12B. Further, unlike the door 11c of the conventional sterilizer, the door 11 of the sterilizer according to the present invention does not require any means for applying pressure thereto from the outside to open or close the door, so that the sterilizer can have a simple construction.

Further, the present invention reduces the number of parts of the sterilizer, which might otherwise cause the sterilizer to malfunction. Due to the reduced number of parts of the sterilizer, the present invention reduces the production cost and maintenance cost of the sterilizer.

As shown in FIG. 3, the body of the sterilizer 1 includes a pressure tank 7, which defines the steam chamber 102 therein and has a steam pressure gauge 41. The opposite ends of the pressure tank 7 are provided with an inlet control valve 42 and an outlet control valve 43, acting as the opening/closing unit.

Further, the steam supply unit 20 includes a pressure regulation valve 21, a steam filter 22, a header 23, electromagnetic valves (air valves) 24, and a flow control valves 25.

Further, each of the pressure regulators 30 comprises an electronic steam discharge valve 31 and a regulation valve 32.

Second Embodiment

Measurement of Temperature Variation

Figures 4, 5:
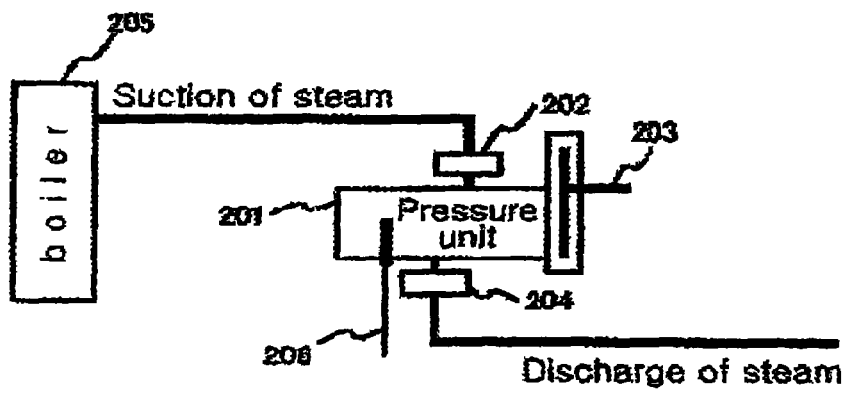
FIG. 4 is a block diagram illustrating the construction of a temperature sensing unit used for sensing temperature variation in a steam chamber of a pressure unit according to another embodiment of the present invention.
FIG. 5 is a diagram illustrating a process of sensing temperature variation in the steam chamber of the pressure unit according to the embodiment of the present invention.
Figure 6:
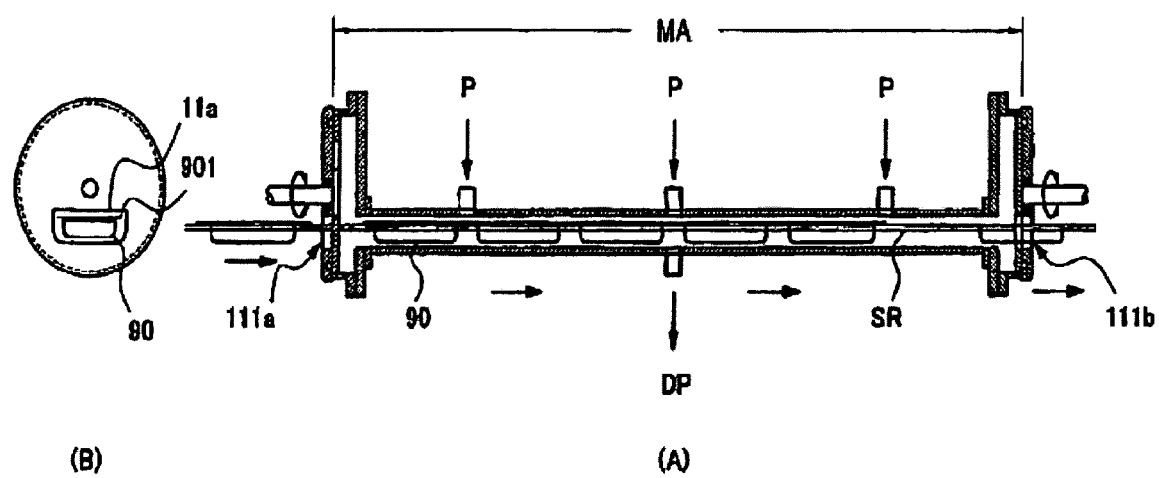
FIG. 6 is a graph illustrating an example of temperature variation sensed in the steam chamber of the pressure unit according to the embodiment of the present invention.
Figure 7:
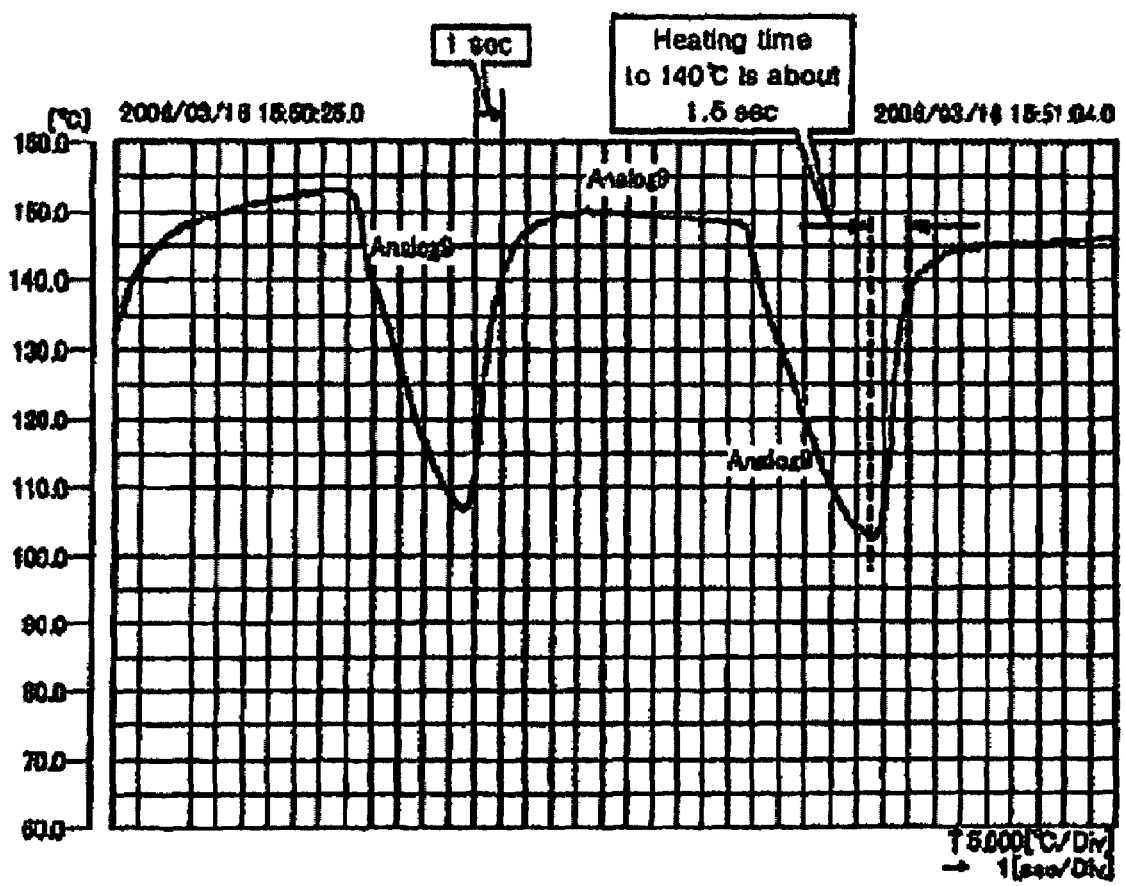
FIG. 7 is a graph illustrating another example of the temperature variation sensed in the steam chamber of the pressure unit according to the embodiment of the present invention.
Figure 8:
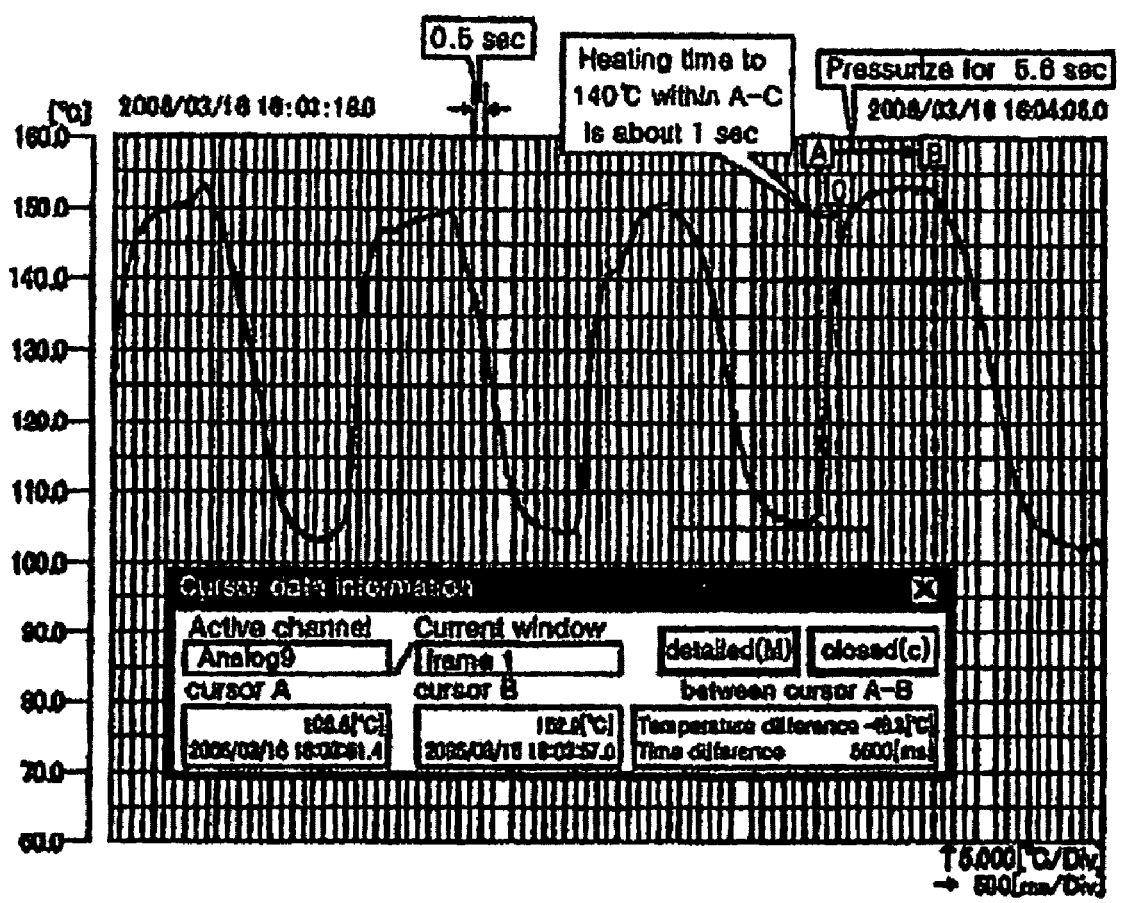
FIG. 8 is a graph illustrating a further example of the temperature variation sensed in the steam chamber of the pressure unit according to the embodiment of the present invention.

FIG. 4 is a block diagram illustrating the construction of a temperature sensing unit used for sensing temperature variation in a steam chamber of a pressure unit 201 according to a second embodiment of the present invention. FIG. 5 is a diagram illustrating a process of sensing the temperature variation in the steam chamber of the pressure unit 201 according to the embodiment of the present invention. FIGS. 6 through 8 are graphs illustrating examples of temperature variation sensed in the steam chamber of the pressure unit 201 according to the embodiment of the present invention.

Hereinbelow, the measurement of temperature variation in the steam chamber of the pressure unit 201 according to the second embodiment of the present invention will be described with reference to FIGS. 4 through 8.

As shown in FIG. 4, the pressure unit 201 includes a hot steam inlet valve 202, which is opened to draw hot steam from a boiler 205 into the pressure unit 201, an opening control valve 203, which opens or closes the opening of the pressure unit 201 so that objects can be inserted into the pressure unit 201 or discharged therefrom, a steam outlet valve 204, which is opened to discharge the steam from the pressure unit 201 to the outside, and a temperature sensor 206.

The temperature variation in the pressure unit 201 was measured through a following process, as shown in FIG. 5.

At first, the opening control valve 203 was closed (S201), and the hot steam inlet valve 202 was opened to draw steam into the pressure unit 201 (S202). Thereafter, the steam was discharged (S203) and the steam outlet valve 204 was closed (S204), and hot steam was drawn into the pressure unit 201 and pressurized (S205). The hot steam inlet valve 202 was closed to maintain the pressurized state (S206) and, thereafter, the steam outlet valve 204 was opened (S207) to discharge the steam from the pressure unit 201 to the outside (S208).

As described above, after the opening control valve 203 was closed (S201), the process (S202 through S208) was executed to finish one cycle. The above process was repeated several times, thus measuring the temperature in the pressure unit 201.

According to the test results of FIG. 6, obtained by repeating the process, it is noted that a time period of about 1.5 seconds is required to increase the temperature from about 100° C. to about 140° C.

According to the test results of FIG. 7, obtained by repeating the process, it is noted that a time period of about 1.0 second is required to increase the temperature from about 100° C. to about 140° C. Further, it is noted that the pressure unit can be continuously pressurized for 5.6 seconds.

According to the test results of FIG. 8, obtained by repeating the process, it is noted that the pressure unit can be continuously pressurized for about 11 seconds at about 140° C.

As described above, the temperature of the pressure unit 201 according to the embodiment of the present invention can be increased from about 100° C. to about 140° C. within a short period of time, which is 1.0 second to 1.5 seconds.

Further, it is noted that the time period for pressurizing the pressure unit can be controlled and the pressure after pressurizing the pressure unit can be reduced within a short period of time.

Described in brief, the temperature of the pressure unit 201 according to the second embodiment of the present invention can be increased to a predetermined point capable of sterilizing food stuffs in a shorter time than can a conventional sterilizer. Further, the temperature of the pressure unit 201 can be reduced to a desired point in a short time. Thus, the present invention remarkably reduces the time period required to sterilize food stuffs in the sterilizer. Further, the present invention can automate the pre-process and post-process of the heat sterilization, so that the work efficiency of the sterilizer can be increased.

Third Embodiment

Figure 9:
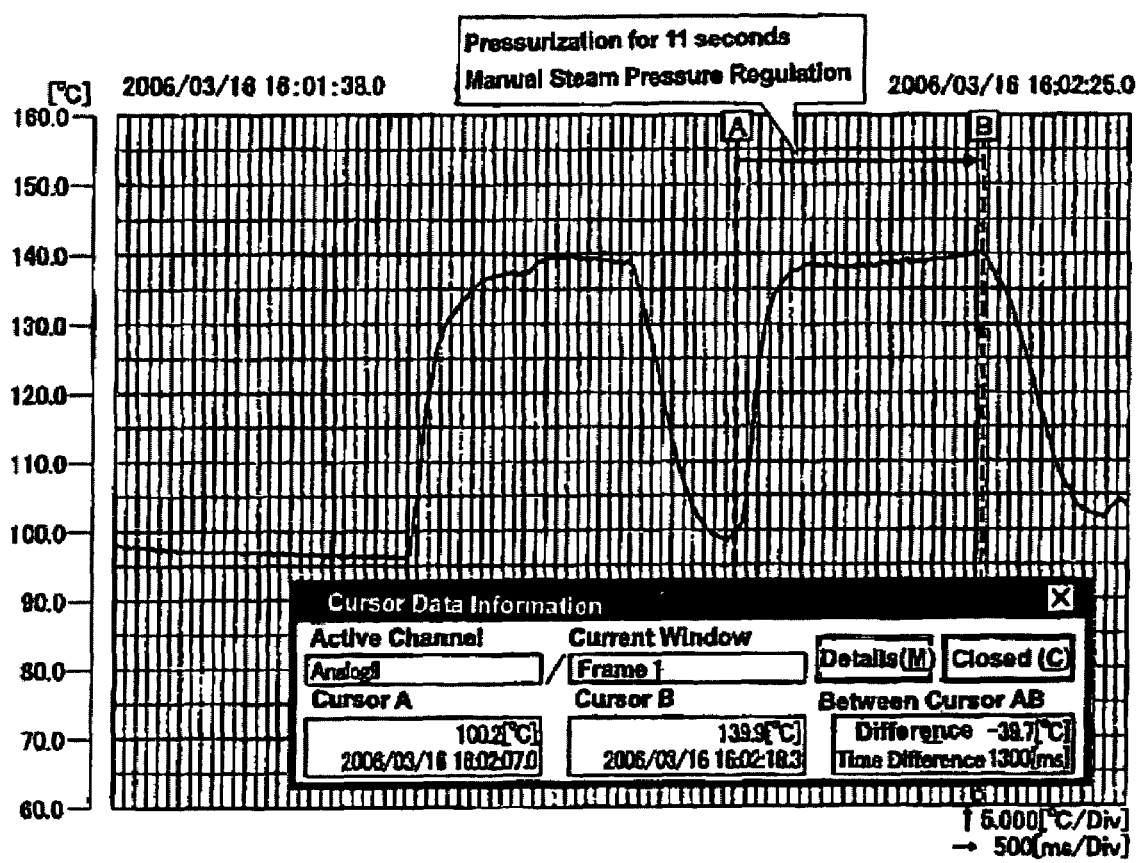
FIGS. 9A and 9B are views illustrating the construction of a sterilizer according to a further embodiment of the present invention.

FIGS. 9A and 9B are views illustrating the construction of a sterilizer 1 according to an embodiment of the present invention, in which FIG. 9A is a plan view of the sterilizer, and FIG. 9B is a left side view of the sterilizer. FIGS. 10A through 10G are views illustrating a sterilization process executed by the sterilizer 1 according to the embodiment of the present invention. FIGS. 11A and 11B are views schematically illustrating the pre-process and post-process of the sterilization of retorted rice using the sterilizer 1 according to the embodiment of the present invention.

As shown in FIGS. 9A and 9B, like the first embodiment, the sterilizer 1 according to the third embodiment includes an opening/closing unit, a steam supply unit P, and a pressure regulator DP. Further, the sterilizer 1 is provided with a guide rail SR, functioning as an inlet/outlet unit for putting a plurality of objects 90 into the steam chamber 102 through an inlet 111a and taking the objects 90 out of the steam chamber 102 through an outlet 111b.

The objects 90, which are provided with respective lids 901 having a width narrower than that of the guide rail SR, are put into the sterilizer 1 through the inlet 111a along the guide rail SR. In the sterilizer 1, predetermined steam pressure P is applied to the plurality of objects 90 in a pressure sterilization region MA, so that the plurality of objects 90 is subjected to heat sterilization at the same time. After the heat sterilization, the objects 90 are discharged from the sterilizer 1 through the outlet 111b. In the present invention, the objects 90 are rectilinearly moved along the guide rail SR, so that the objects 90 can be sequentially subjected to heat sterilization by the sterilizer 1 in an automated plant.

Figure 10:
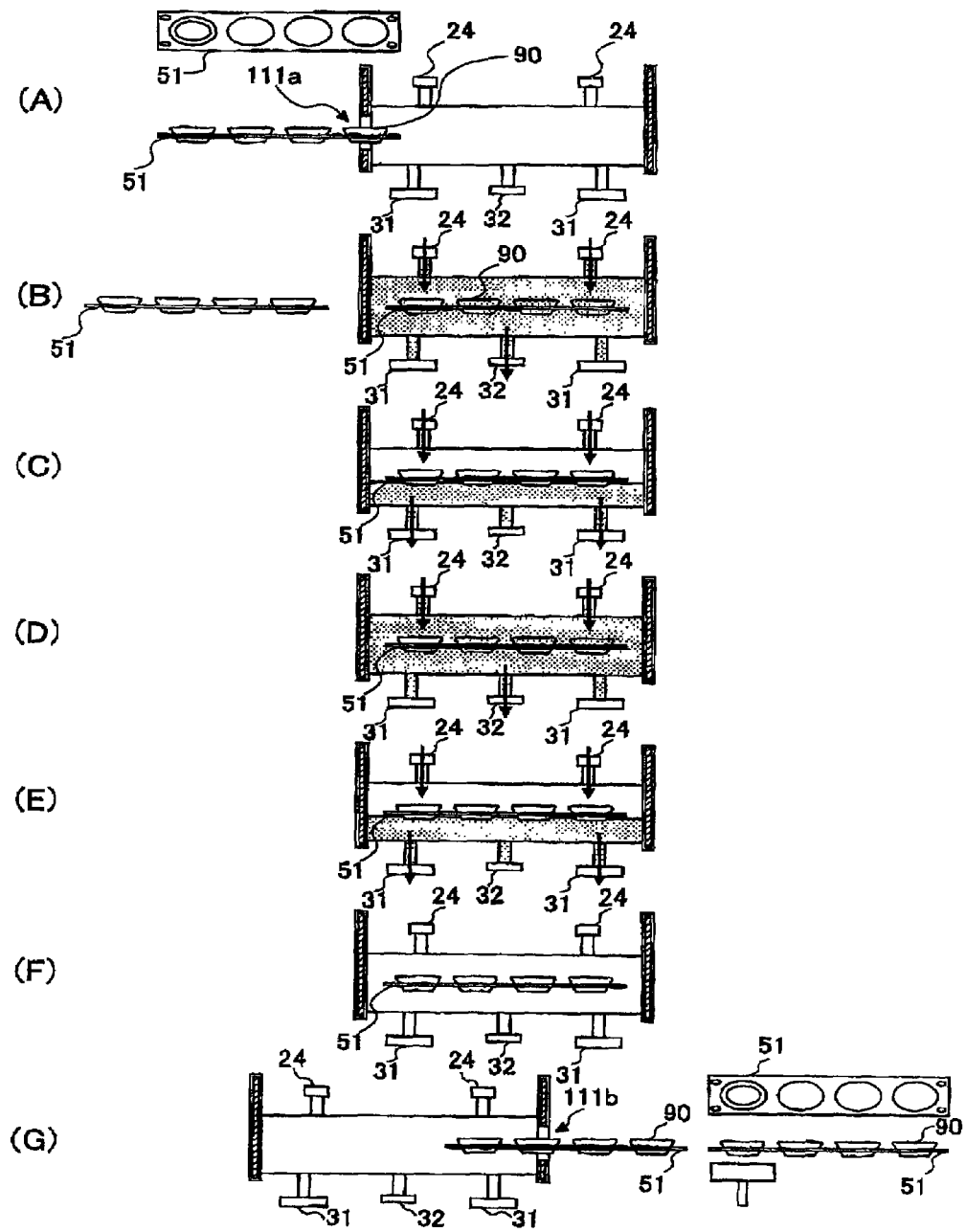
FIGS. 10A through 10G are views illustrating a sterilization process executed by the sterilizer according to the embodiment of the present invention.
Figure 11:
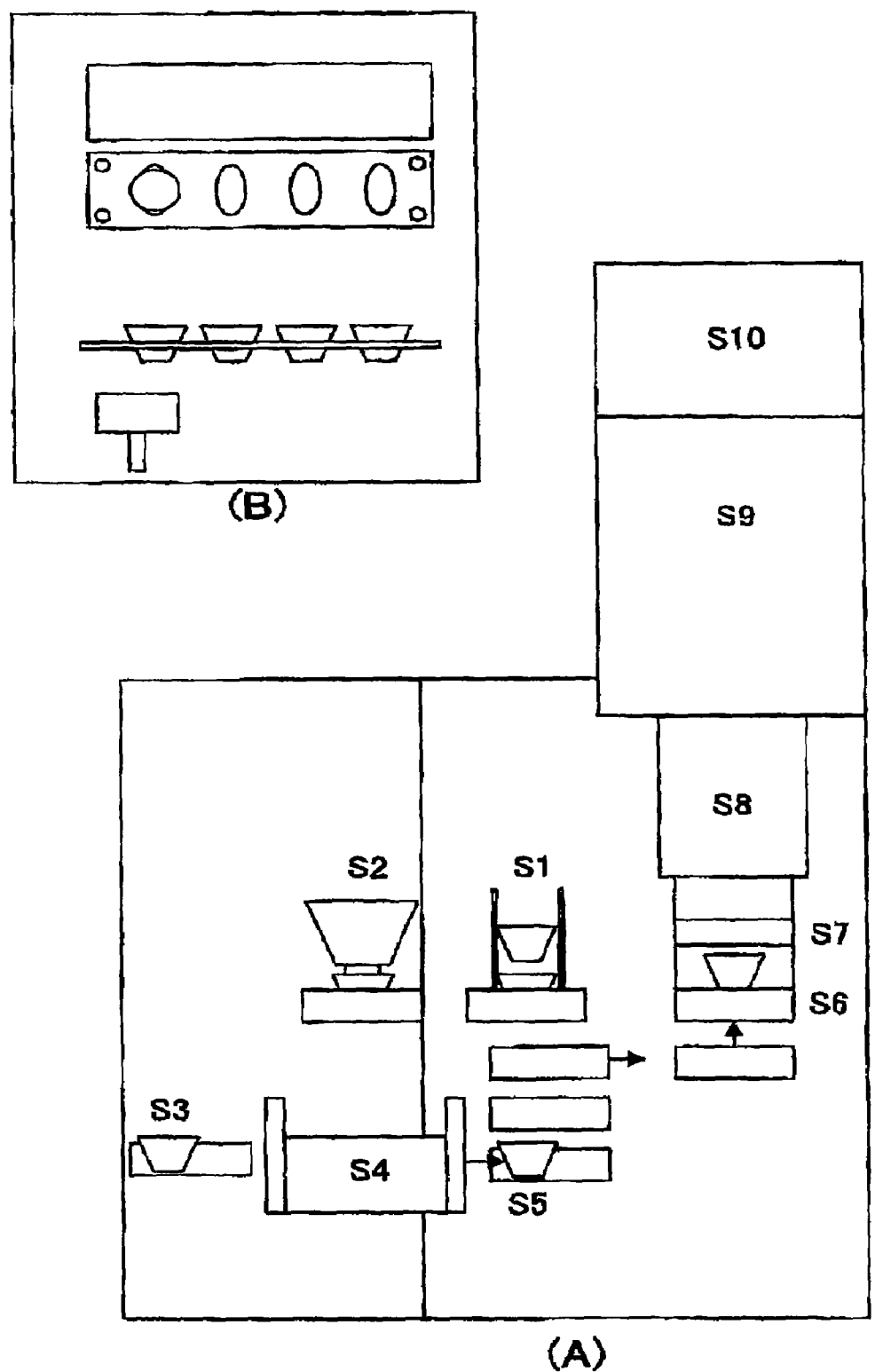
FIGS. 11A and 11B are views schematically illustrating the pre-process and post-process of the heat sterilization of retorted rice using the sterilizer 1 according to the embodiment of the present invention.

In the sterilization process of the sterilizer 1 according to the third embodiment of the present invention, the objects 90 loaded on respective feed plates 51 are sequentially put into the steam chamber of the sterilizer 1 through the opened inlet 111a, as shown in FIG. 10A.

Thereafter, as shown in FIG. 10B, the inlet 111a is closed and the electromagnetic valves (air valves) 24 are opened, so that steam having a predetermined pressure is supplied to the steam chamber. The steam chamber of the sterilizer 1 is retained at a temperature not lower than a predetermined point for a predetermined long period of time, thus sterilizing the objects 90. Here, the steam having a predetermined pressure may be supplied from the regulation valve 32 along with air.

Thereafter, as shown in FIG. 10C, the electromagnetic valves (air valves) 24 are closed, while the electronic steam discharge valves 31 are opened, thus regulating the steam pressure of the steam chamber to a predetermined steam pressure.

Thereafter, as shown in FIG. 10D, the electronic steam discharge valves 31 are closed, and the electromagnetic valves (air valves) 24 are opened, thus pressurizing the steam chamber by supplying a predetermined steam pressure to the steam chamber.

Thereafter, as shown in FIG. 10E, pressure regulation is executed in the same manner as that described for FIG. 8.

After the pressure regulation, the electronic steam discharge valves 31 are opened after a predetermined long period of time has passed, as shown in FIG. 10F, thus discharging the pressurized steam from the steam chamber.

After heat has been discharged from the pressure tank 7, the outlet 111b is opened and the objects 90 are discharged from the steam chamber along with the feed plates 51, as shown in FIG. 10G.

Hereinbelow, a sterilization process for sterilizing retorted rice using the sterilizer 1 according to the third embodiment of the present invention will be described. In the pre-process and post-process for sterilizing the rice using the sterilizer 1, a container for containing rice therein is supplied at step S1, as shown in FIGS. 11A and 11B.

At step S2, washed rice is put into the container.

Thereafter, the container is moved to a feed plate at step S3.

At step S4, the washed rice contained in the container is sterilized by the sterilizer 1 according to the embodiment of the present invention.

The container, containing the sterilized rice therein, is moved to the feed plate at step S5.

At step S6, the container, containing the sterilized rice therein, is moved to the inlet of a sealing unit.

At step S7, water is put into the container.

At step S8, the container, containing the sterilized rice therein, is moved to the sealing unit.

At step S9, the sterilized rice contained in the container is moved to a cooking unit, thus being cooked by the cooking unit.

At step S10, the sterilized and cooked rice in the container is placed in a refrigeration unit.

As is apparent from the above description, the sterilizer according to the present invention provides advantages in that it automatically and sequentially executes the sterilization process, and thus the sterilization process from the supply of containers to the discharge of products can be automated.

In the embodiment of the present invention, the objects are automatically put into or taken out of the sterilizer 1 while being loaded on respective feed plates. Thus, the sterilization process of the sterilizer according to the present invention can be automatically executed.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A sterilizer comprising a hermetic container, which defines therein a steam chamber for conducting the heat sterilization of objects contained therein, wherein the hermetic container comprises:

a steam supply unit for supplying hot steam having a predetermined pressure to the steam chamber; and a cylindrical container body comprising end plates on each end of said cylindrical container body, wherein at least one of said end plates comprises an opening/closing unit for covering the end of the container body, wherein the opening/closing unit comprises an opening for passing the objects there through and a door for closing the opening from an inside of the steam chamber, wherein the door is moved to come into contact with the opening from the inside of the steam chamber and steam pressure inside the steam chamber is increased by the steam supply unit, so that the door is brought into close contact with the opening, thereby hermetically sealing the steam chamber, characterized in that the door is eccentrically connected to an inner end of a rotating shaft, wherein the rotating shaft passes through the opening of the end plate, such that the door can be eccentrically rotated parallel to the opening of end plate by the rotating shaft.

2. The sterilizer according to claim 1, wherein the opening is defined by a tapered circular edge, a diameter of which is reduced in a direction from the inside to an outside of the steam chamber, and the door comprises a frusto-conical part at an end thereof, wherein the frusto-conical part of the door comes into close contact with the tapered circular edge of the opening.

3. The sterilizer according to claim 1, wherein the opening/closing unit is manipulated outside the hermetic container, and opens or closes the opening with the door.

4. The sterilizer according to claim 1 or 2, wherein the objects are put into the container body through the opening of one of two opening/closing units provided in opposite ends of the container body, and are taken out of the container body through the opening of a remaining opening/closing unit.

5. The sterilizer according to claim 4, further comprising:

an inlet unit for sequentially putting the objects into the steam chamber through the opening of one of the opening/closing units; and an outlet unit for sequentially discharging the objects from the steam chamber through the opening of the remaining opening/closing unit, wherein the opening/closing units are operated in conjunction with both the inlet unit and the outlet unit, thus opening or closing the respective openings.

6. The sterilizer according to claim 4, wherein the door is supported by a rotating shaft, which passes through the opening, such that the door is rotatable and movable inwards and outwards, wherein an end of the rotating shaft is eccentrically connected to the door.

7. The sterilizer according to claim 5, wherein the door is supported by a rotating shaft, which passes through the opening, such that the door is rotatable and movable inwards and outwards, wherein an end of the rotating shaft is eccentrically connected to the door.

* * * * *